United States Patent [19]

Sumi et al.

[11] Patent Number: 4,942,618

[45] Date of Patent: Jul. 17, 1990

[54] METHOD AND APPARATUS FOR DETERMINING THE SHAPE OF WIRE OR LIKE ARTICLE

[75] Inventors: Kazuhiko Sumi; Manabu Hashimoto; Yoshikazu Sakaue; Kazuo Aita; Masahiro Sasakura; Yutaka Ozaki, all of Amagasaki, Japan

[73] Assignee: Mitsubishi Denki Kabushiki Kaisha, Tokyo, Japan

[21] Appl. No.: 324,185

[22] Filed: Mar. 16, 1989

[51] Int. Cl.[5] .................... G06K 9/00

[52] U.S. Cl. .................... 382/8; 356/376; 356/381; 356/384; 356/387; 382/62

[58] Field of Search .................... 382/8, 62; 356/376, 356/381, 384, 387

[56] References Cited

U.S. PATENT DOCUMENTS 4,199,253 4/1980 Ross .................... 356/376

OTHER PUBLICATIONS

Nikkei Electronics, May 16, 1988, No. 447 p. 99.

A. L. Pal, et al. "A Feasibility Study, ect." Journal of Rabotic Systems, 5 (2), 147–179 (1988).

*Primary Examiner*—Leo H. Boudreau
*Assistant Examiner*—Daniel Santos
*Attorney, Agent, or Firm*—Thomas R. Morrison

[57] ABSTRACT

A method and apparatus for determining the shape of a wire or like article is provided in which a plurality of image pickup means are provided that view the wire through coaxial optical systems having their focal planes positioned differently from each other, the wire images imaged on the respective image pickup means are processed to determine the contrast and size of the images, and the results are used to determine the shape of the spatially disposed wire or the like.

2 Claims, 17 Drawing Sheets

$$\Delta \ell = \frac{A - B}{2 \sin \alpha}$$

METHOD AND APPARATUS FOR DETERMINING THE SHAPE OF WIRE OR LIKE ARTICLE

This invention relates to a method and apparatus for determining the shape of a wire or like article, and, more particularly, to a technique for determining the shape of wires or like articles spanned in a space and also to a wire-like article bond inspecting apparatus for inspecting bonding of wires or the like used for wiring in, for example, integrated circuits (IC's).

BACKGROUND OF THE INVENTION

FIG. 1 shows an arrangement for explaining a conventional technique of determining the positioning of a wire or like article (hereinafter referred to simply as wire) which is shown in, for example, the digest of technical papers, G-78, for the 1986 joint meeting of the electrical and electronic societies of Western Japan. The arrangement comprises an objective lens 1, an image pickup device (camera) 3 which converts into an electrical signal the image of a wire 5 imaged on the pickup device 3 by the objective lens 1, an image processor 4 for processing the video signal supplied from the pickup device 3, and a movable base 6 for moving the wire 5 which is placed thereon in the field of the objective lens 1.

In operation, the image of the wire 5 on the movable base 6 of which the shape is to be determined is imaged on the imaging surface at the pickup device 3 by the objective lens 1. Since the wire 5 has the shape which varies three-dimensionally, only those portions of the wire 5 which lie in the focal plane 100 determined by the distance of the imaging surface of the pickup device 3 from the objective lens 1 and the focal length of the objective lens 1, are imaged with high contrast and the remaining portions of the wire 5 are defocused. When the movable base 6 is moved up or down, different portions of the wire 5 come to lie in the focal plane 100 successively.

The video signal provided by the image pickup device 3 is applied to the image processor 4 which extracts the contrast between the image of the wire 5 and the background. For each of locations on the imaging surface, (called "pixels" when digital image processing is to be provided), the position of the movable base 6 where maximum contrast is formed at that location is determined from the image data obtained through the image processing in the processor 4, and the thus determined positions of the base 6 are stored. This processing is repeated with the base 6 being moved in small steps in either one of the directions indicated by arrows in FIG. 1. After the completion of the processing over the range of movement of the base 6, the height of the wire 5 or the levels of respective portions of the wire 5 can be calculated from the values of the stored positions of the base 6.

The above-described method for determining the shape of a wire or like article is time-consuming, because the movable base 6 must be moved in small steps and for each position thereof, imaging and image processing must be made. Another disadvantage of this method is that because it is time-consuming, the method cannot determine the shape of the wire 5 when it changes in shape in time or when it is moving.

One example of apparatus for detecting a wire or like article is shown in FIG. 2. The apparatus is a well-known wire bond inspecting apparatus disclosed in unexamined Japanese Patent Publication No. SHO 60-49212. This apparatus comprises a rotary base 41. An IC 42 to be inspected is placed on the base 41. Two TV cameras 43 and 44 are mounted above and diagonally with respect to the base 41. The cameras 43 and 44 are in mutually opposing positions with the base and, hence, the IC thereon being intermediate between them.

The IC 42 is placed in position on the rotary base 41, and it is imaged simultaneously on the two TV cameras 43 and 44. FIG. 3 shows two images provided by the apparatus of FIG. 2. From these two images, the lateral displacement of a wire 45, $\Delta l$, from a reference line is determined from an equation $\Delta l=(A-B)/2\sin\alpha$ as shown.

In the arrangement shown in FIGS. 2 and 3, an article is picked up in diagonal directions by the two TV cameras, and the wire shape is determined from the parallax of corresponding portions of the wire derived from the two images. Accordingly, in case that a number of wires are densely arranged or wires of like shape are spanned in parallel with each other, it is difficult to detect the same desired wire in the two image, or wires of interest to be inspected may be hidden behind adjacent wires so that useful inspection cannot be made.

SUMMARY OF THE INVENTION

An object of the present invention is to provide a method of determining the shape of a wire or wire-like article by a single image entry processing, which can eliminate problems of conventional wire-shape determining methods as stated above.

According to the method of the present invention, a plurality of image pickup devices are used. The image pickup devices are so arranged to have their focal planes in different positions and to cover the same field of view. For each of the images of a wire picked up by the respective pickup devices, contrast evaluation and wire width determination are carried out, to thereby identify intersections of the wire with the respective focal planes and deviation of other wire portions from a respective one of focal planes. The thus obtained measurements for the respective focal planes are appropriately combined for computation of the shape of the wire.

Another object of the present invention is to provide a wire bonding inspection apparatus which is free of problems seen in the above-stated conventional wire bond inspection apparatus. The wire bond inspection apparatus according to the present invention can detect locations of closely spaced wire bonds, and also can detect three-dimensional features of a wire such as bending at a neck portion of the wire and sagging and tilting of the wire, and can inspect misplacements of wire bonds such as ball bonds and stitch bonds.

The wire bond inspection apparatus according to the present invention comprises a plurality of image pickup means which have differently positioned focal planes and which, however, pick up the same wire or like article through coaxial optical systems. The apparatus further comprises illuminating means having an optical axis coincident with the optical axis of the coaxial optical systems, for illuminating the wire, diagonally illuminating means for directing light diagonally toward the wire, control means for controlling the timing of the illumination of the wire by the coaxially and diagonally illuminating means, image storing means for digitizing the output of the plurality of image pickup means and storing the digitized output in a plurality of image memory locations of said image storing means, an image processing unit for reading the contents of the image storing means and determining the position of the top of the curve of the wire, the angles between the wire and the focal planes at their intersections, and the lateral displacement of the wire, and a judgement unit utilizing the measurements provided by the image processing unit to judge whether the wire bonds are acceptable or not.

DETAILED DESCRIPTION OF THE INVENTION

Figure 1:
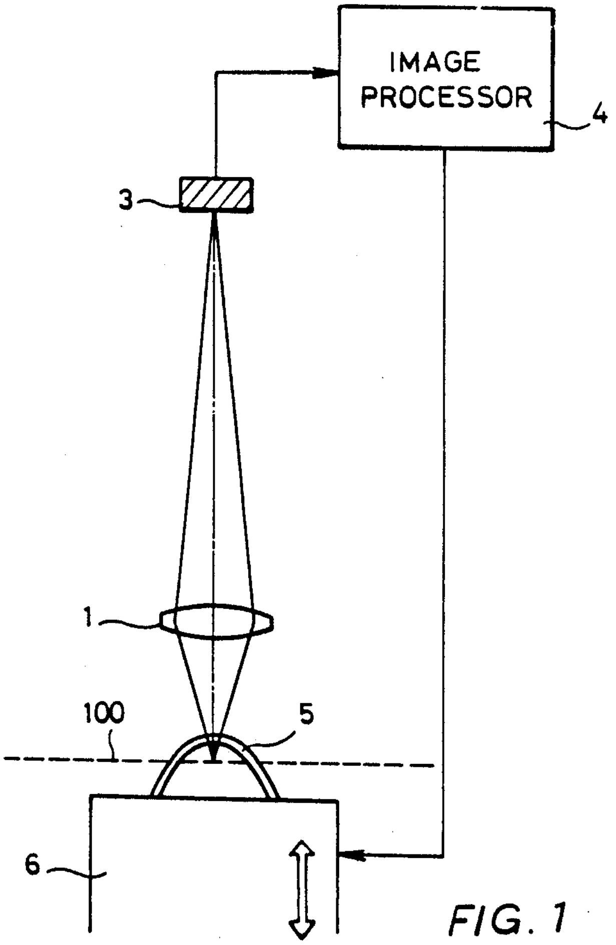
FIG. 1 is an illustration for use in explaining a conventional apparatus for determining the shape of a wire or like article.
Figure 2:
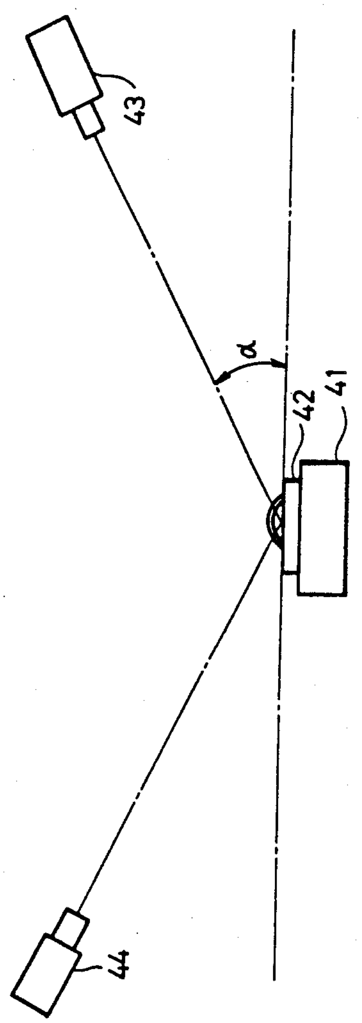
FIG. 2 is a side view of a conventional wire bond inspection apparatus.
Figure 3:
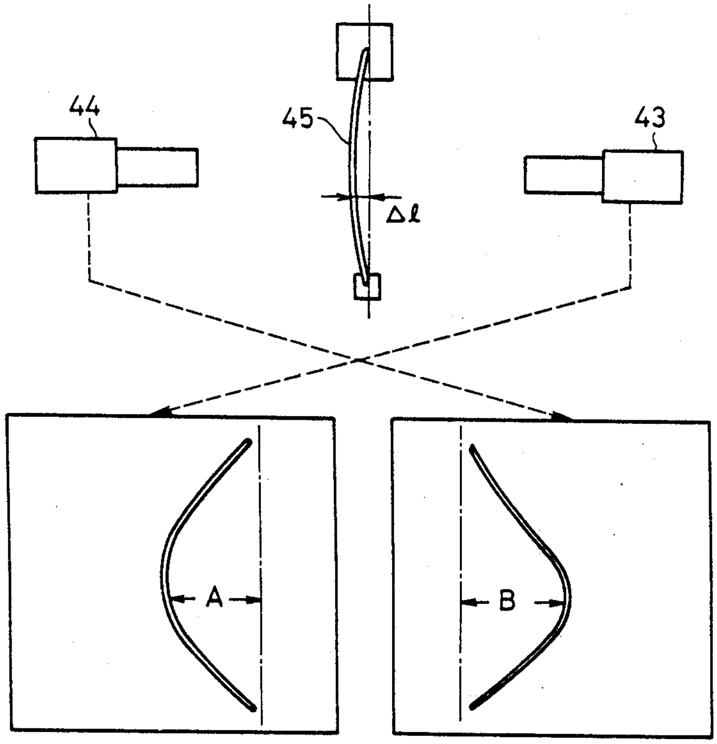
FIG. 3 shows the positional relationship between the wire and the image pickup devices of FIG. 2 and the images picked up by the pickup devices.
Figure 4:
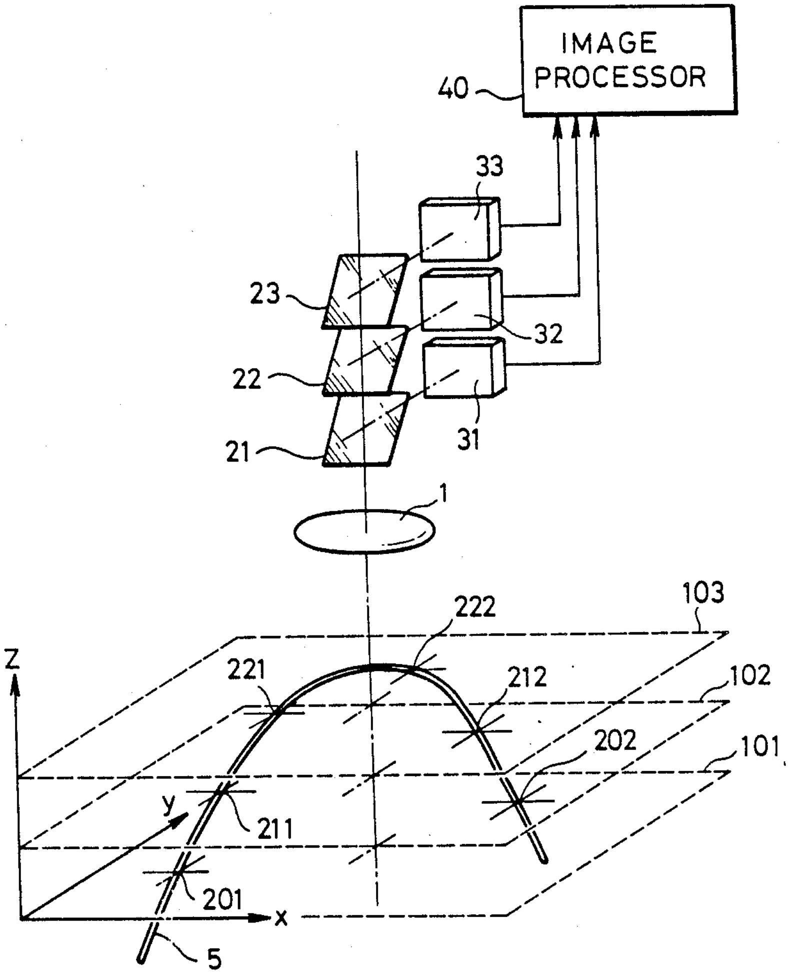
FIGS. 4 and 5 are perspective and side views, respectively, of an exemplary arrangement for carrying out the wire shape determining method according to one embodiment of the present invention.
Figure 5:
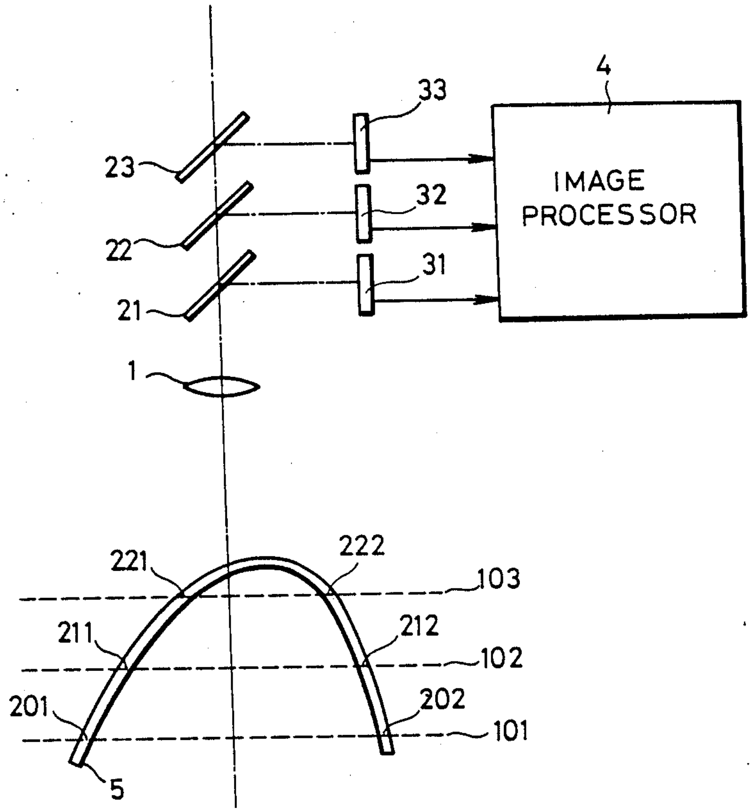

Now, one embodiment of the present invention is described with reference to the accompanying drawings. In FIGS. 4 and 5, there is provided an objective lens 1. Half-mirrors or partially transparent mirrors 21, 22 and 23 are disposed on the optical axis of the objective lens 1. Image pickup devices 31, 32 and 33 are disposed on the optical axes of light reflected by the respective half-mirrors 21, 22 and 23, and the image pickup devices provide image signals to an image processor unit 40 which processes the image signals and determines the shape of a wire or like article 5 picked up by the pickup devices through arithmetic operation.

Figure 6:
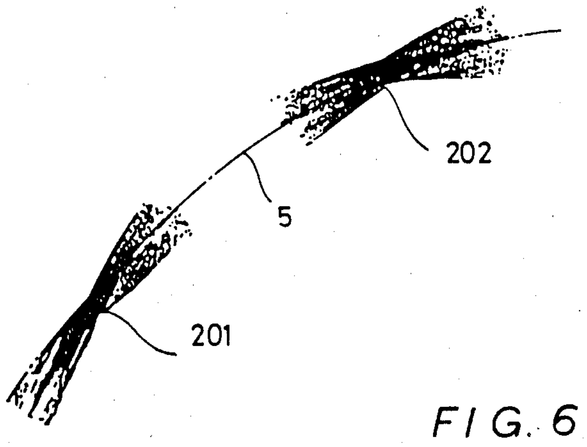
FIGS. 6, 7 and 8 show images picked up by the respective image pickup devices shown in FIG. 4.
Figure 7:
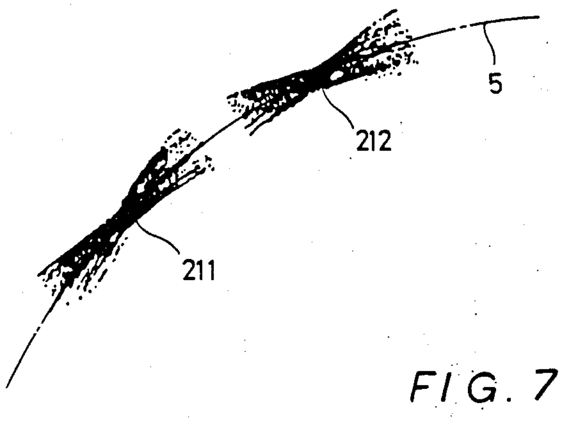
Figure 8:
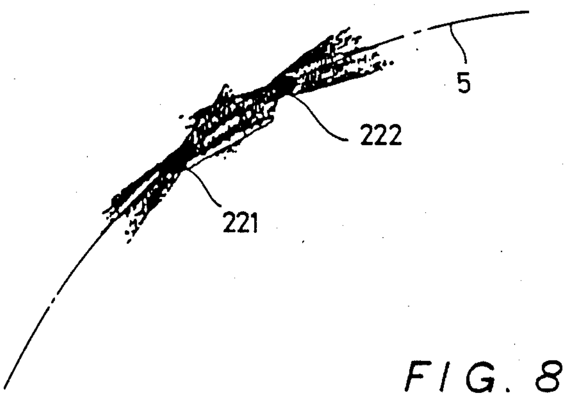
Figure 9:
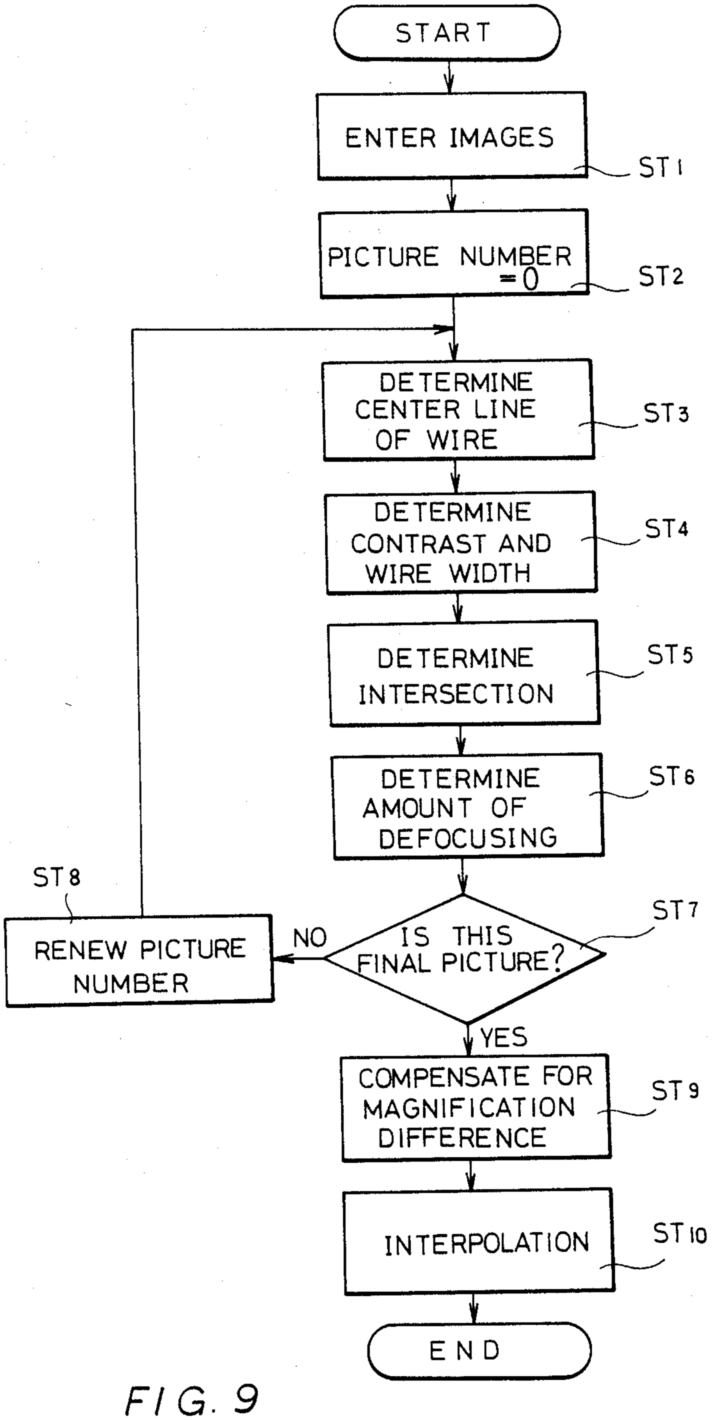
FIG. 9 is a flow chart for the wire shape determining method according to the present invention.
Figure 10:
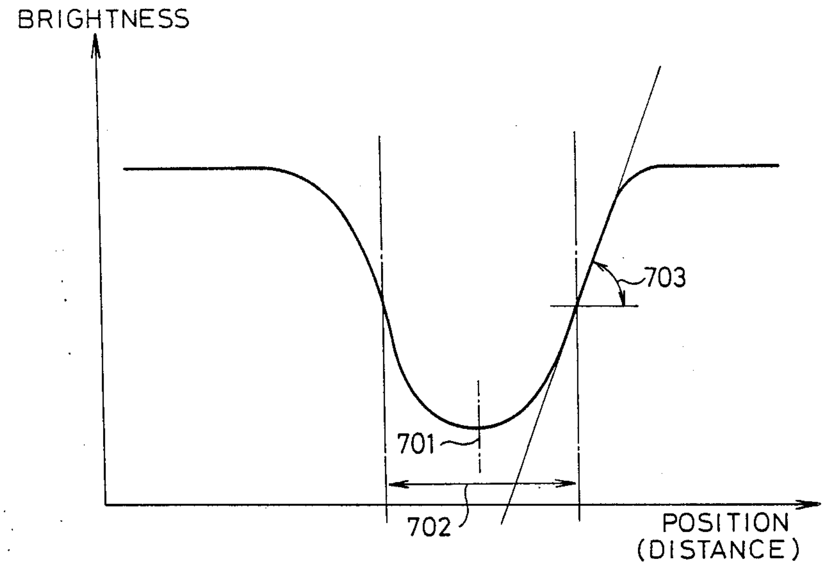
FIG. 10 is a varying brightness pattern showing the relationship between the width of the wire and the image contrast.

In operation, the image of the wire 5 is imaged on the imaging surfaces of the respective image pickup devices 31–33 through the objective lens 1 and the respective half-mirrors 21–23. The optical distances of the pickup devices 31, 32 and 33 from the objective lens 1 are different from each other. Accordingly, if an article is in a plane 101, it is imaged on the pickup device 31, if an article is in a plane 102, it will be imaged on the pickup device 32, and if an article is in a plane 103, it will be imaged on the pickup device 33. As shown in FIG. 4, however, the wire 5 is positioned to intersect with the respective planes 101–103. Accordingly, on the image pickup devices 31–33, the wire is imaged as shown in FIGS. 6, 7 and 8, respectively. The image on each of the pickup devices has a minimum width and maximum contrast at the portion corresponding to the wire intersection with the respective one of the planes 101–103. In the image processor unit 40, the images shown in FIGS. 6, 7 and 8 provided by the respective pickup devices 31, 32 and 33 are applied to frame memories, and the image processing is carried out in accordance with a flow chart such as shown in FIG. 9. More specifically, in Step $ST_1$, the image signals from the image pickup devices 31–33 are applied to the frame memories, and, in Step $ST_2$, the picture number is set to zero. Next, in Step $ST_3$, the image data stored in the frame memories is processed to search the shape of the wire, and the longitudinal center line of the wire is determined. For example, when the wire is illuminated from below, the images applied to the frame memories are dark relative to the background, as shown in FIGS. 6–8. (Of course, articles to be detected can be illuminated from above.) By tracing a minimum brightness point in each of the images, the longitudinal center line 701 (FIG. 10) of the wire can be determined. In step $ST_4$, the brightness variation in the wire width direction is measured, and a brightness variation pattern as shown in FIG. 10 is developed. From this brightness variation pattern, the width 702 and the contrast 703 of the wire image are determined. Such values are dependent on the amount of displacement of an article from a focal plane, and, therefore, if the actual width of the wire is known and constant, the amount of displacement can be calculated from the image width 702. Next, in Step $ST_5$, the intersection of the wire 5 with the respective one of the focal planes is detected by searching the point of the wire image at which the width of the image is equal to the actual wire width and at which a maximum contrast is exhibited. In Step $ST_6$, for each of the focal planes, the amount of displacement of each of points in the vicinity of the intersection form that focal plane is measured. Next, in Step $ST_7$, judgment as to whether the thus processed picture is the final picture or not is made. If NO, the picture number is incremented in Step $ST_8$ and the processing returns to Step $ST_3$. The above-stated sequence of processing is executed for each image from each of the image pickup devices 31, 32 and 33, whereby, for each of the focal planes, the intersection of the wire with that focal plane and the amount of displacement of each of points of the wire in the vicinity of that intersection from that focal plane are determined.

When the processing for the determination of the respective intersections and the amounts of displacement is completed for the final picture, the judgment of YES is made in Step $ST_7$, and the processing advances to Step $ST_9$. In Step $ST_9$, compensations for differences in magnification factor and mutual displacements of the center axes of the pickup devices 31–33 are made, and, then, the respective pictures are superimposed with each other to judge the shape of the wire. More specifically, an article of known size and shape is picked up by the respective image pickup devices 31, 32 and 33 beforehand, and displacements of the same point in the respective pictures and also difference in magnification or reduction factor of the pickup devices are measured. These values are used to compensate for the difference in magnification factor and for the center displacement among the image pickup devices in Step $ST_9$. Then the processing advances to Step $ST_{10}$. In Step $ST_{10}$, the respective intersections of the wire 5 with the focal planes are determined, and the intersections are connected to each other through calculation of the wire portions between the intersections, from the above-determined amounts of displacement of points near the intersections from the respective ones of the focal planes. Thus, the processing is completed, and the entire shape of the wire has been determined in a simple way.

Figure 11:
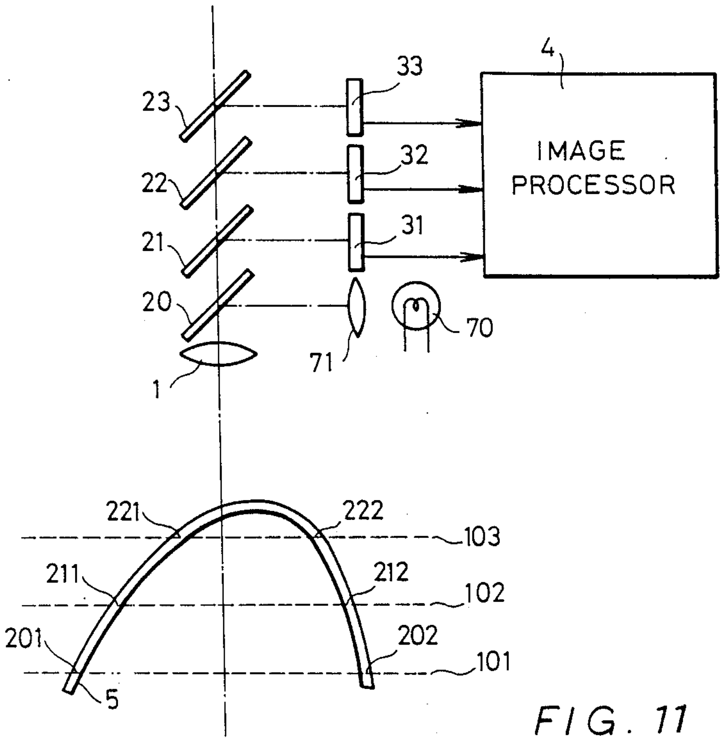
FIGS. 11, 12 and 13 show some of various possible locations of the illuminating means which can be used for carrying out the method according to the present invention.
Figure 12:
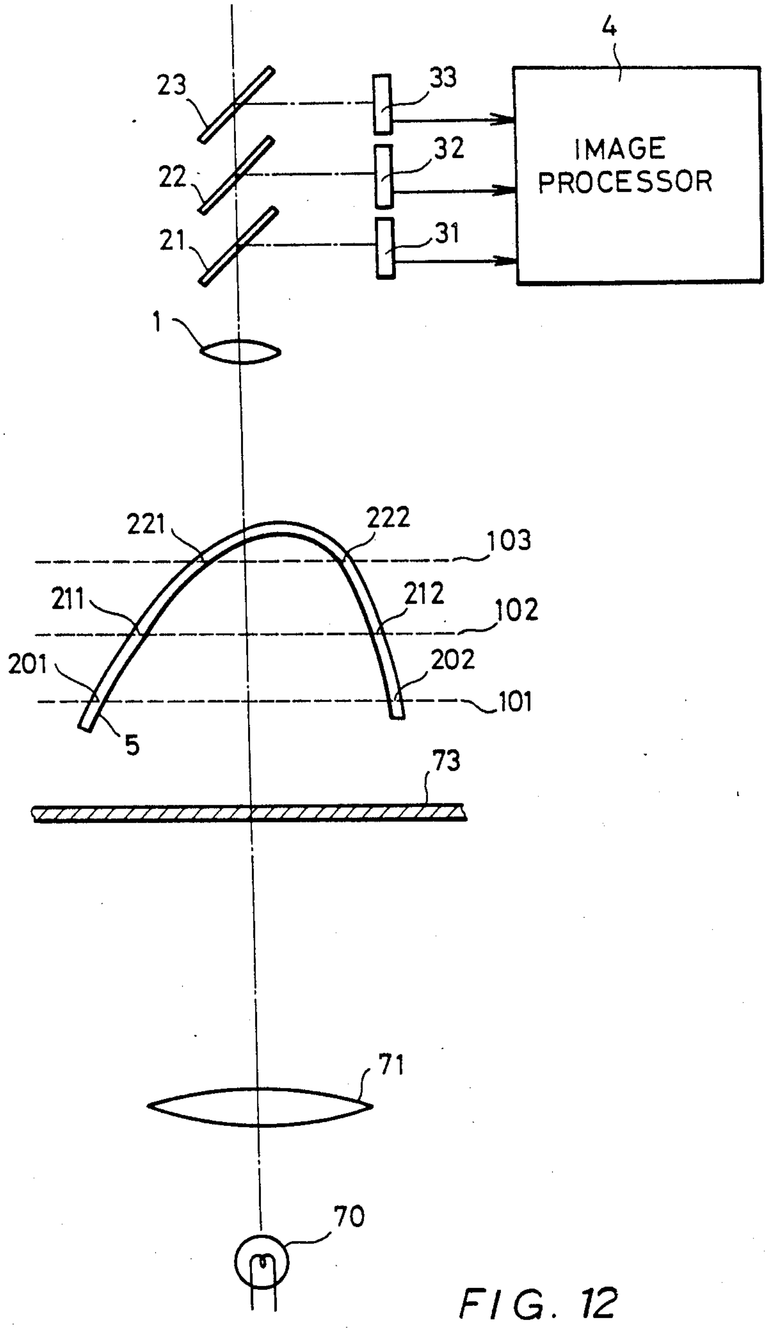
Figure 13:
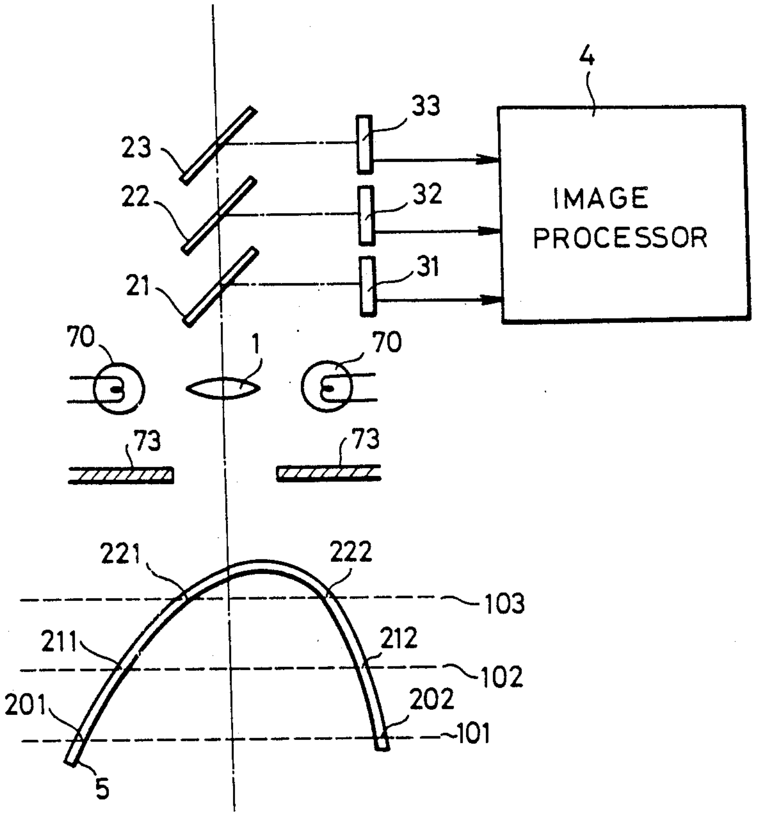

In the above-described embodiment, no special illumination is employed. However, for better derivation of contrast variations, coaxial illumination such as shown in FIG. 11 may be used. In FIG. 11, another half mirror 20 is disposed on the axis of the objective lens 1, and light from an illumination source 70 is condensed by a condenser lens 71 and then supplied to the half-mirror 20 to illuminate the wire 5. Alternatively, transmissive illumination such as shown in FIG. 12 may be used, in which light emitted from the source 70 is condensed by the condenser lens 71, and the light then passes through a diffusion plate 73 and illuminates the wire 5 from below. If the background is too dark to use transmissive illumination, diffuse illumination as shown in FIG. 13 may be used, in which illumination sources are disposed symmetrically with respect to the optical axis of the objective lens 1, and light from the illumination sources is diffused by means of a diffusion plate 73. The thus diffused light is used to illuminate the wire 5, whereby a bright image of the wire 5 with a dark background is obtained.

Furthermore, in the above-described embodiment, half-mirrors are used for splitting optical paths, but other suitable means such as prisms may be used. The same effects can result even if another suitable optical systems such as one in which an initial optical path is split into two and each of the two split paths is again split into two, which results in four optical paths, are used.

In order to increase the precision of determination in the depth direction the number of the image pickup devices may be increased, or, alternatively,the spacing between adjacent focal planes 101, 102 and 103 may be made variable so as to provide measurements in two steps.

As described, according to the present invention, an article of interest having portions lying in a plurality of focal planes is simultaneously picked up by image pickup devices. Accordingly, it is no longer necessary to change the distance between the article and an image pickup device as in conventional arrangements, whereby the processing speed can be increased. Furthermore, the shapes of wires or like articles which vary in time can be easily determined.

Figure 14:
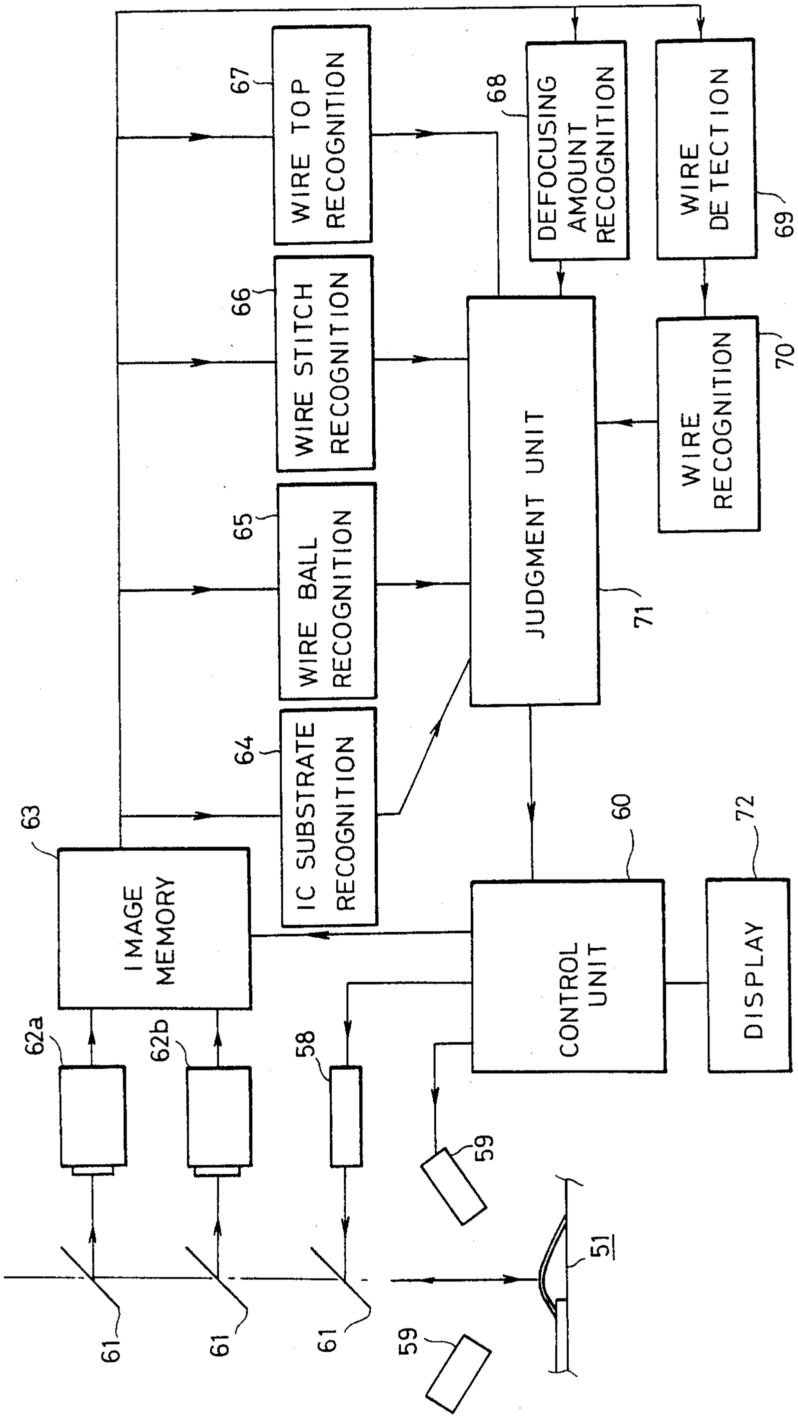
FIG. 14 is a block diagram of a wire bond inspection apparatus according to the present invention.
Figure 15:
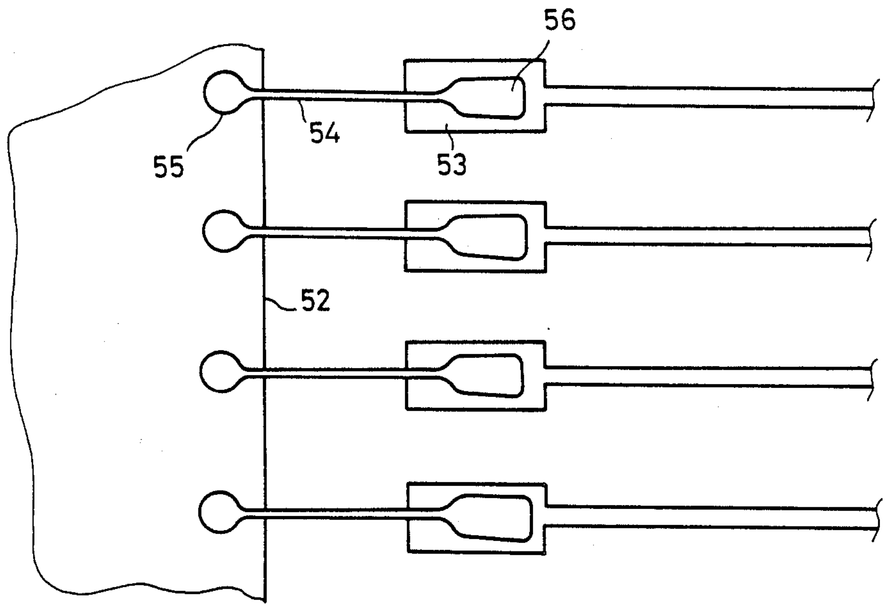
FIG. 15 and 16 are schematic plan and side views of part of articles to be inspected.
Figure 16:
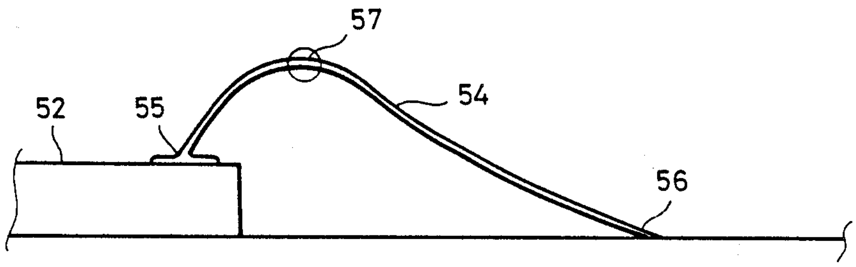

Next, a wire bond inspection apparatus according to the present invention is described with reference to FIGS. 14–23. FIG. 14 is a block diagram of a wire bond inspection apparatus according to the present invention. FIGS. 15 and 16 are plan and side views of part of an item to be inspected, respectively. In FIGS. 14–16, there is shown a thermal printer head 51 as an example of item to be inspected. The thermal printer head 51 comprises an IC chip 52 on a substrate and bonding pads 53, between which wires 54 are spanned. The end of each wire 54 on the IC side comprises a wire ball 55 and the other end comprises a wire stitch 56. As shown in FIG. 16, the surface of the IC chip 52 is at a higher level than the wire stitch 56. The wire 54 has a relatively flat portion 57 which is highest in level (hereinafter referred to as wire top portion). In the illustrated embodiment, the item 51 to be inspected is illuminated by a downcast illumination device 58 (FIG. 14) and diagonal illumination devices 59 (FIG. 14). The downcast light produces contrast among the wire 54, the wire ball 55 and the IC chip 52, and also contrast among the wire 54, the wire stitch 56 and the bonding pad 53. The diagonal illumination produces contrast between the wire top portion and the remaining portions of the wire. The timing of the emission of light from the downcast illumination device 58 and the diagonal illumination devices 59 is controlled by a control unit 60. Thus, a plurality of images of desirable contrast can be obtained for each portion of the wire. Half-mirrors 61 are used to split light reflected from the item to be inspected so as to be incident on a TV camera-A **62*a* having its focal plane at the same level as the IC chip surface, and also incident on a TV camera-B 62*b* which is in the optical system coaxial with that of the camera-A 62*a* and has its focal plane at the same level as the substrate surface. As shown in FIG. 14, the optical axes of the TV cameras 62*a* and 62*b* are coaxial with the optical axis of the downcast illumination device 58. Signals from the TV cameras are digitized and stored in an image memory 63**.

Figure 17A:
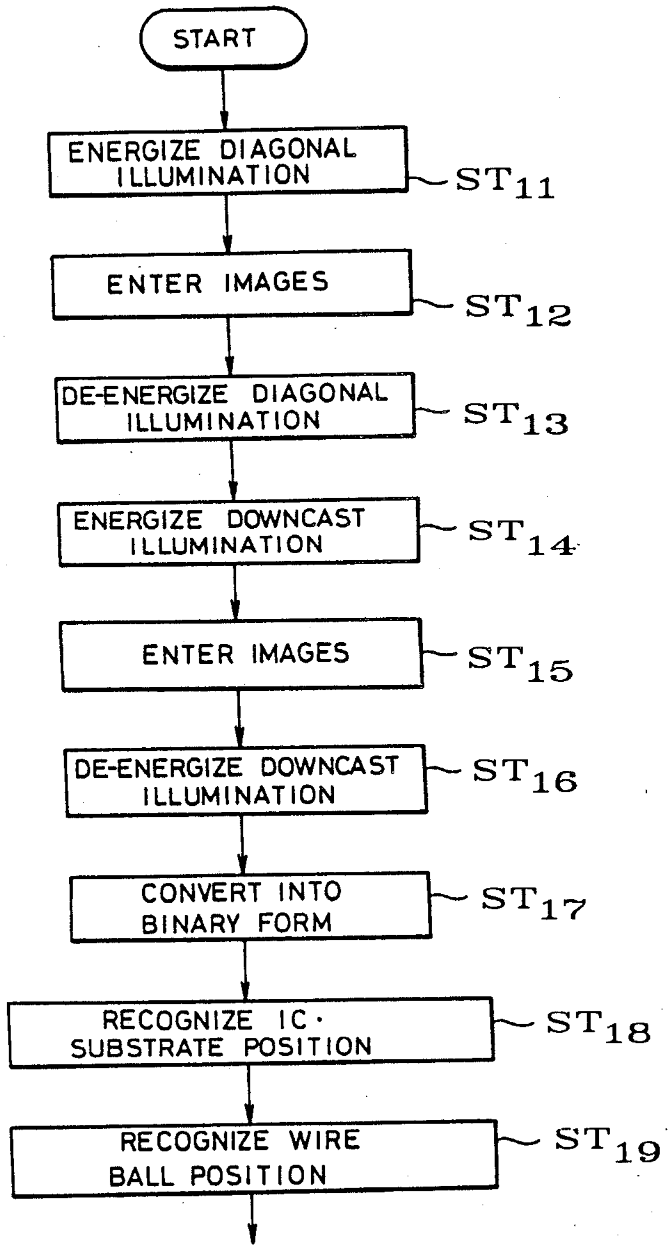
FIGS. 17*a* and 17*b* are a flow chart for use in explaining the operation of the wire bond inspection apparatus of FIG. 14.
Figure 17:
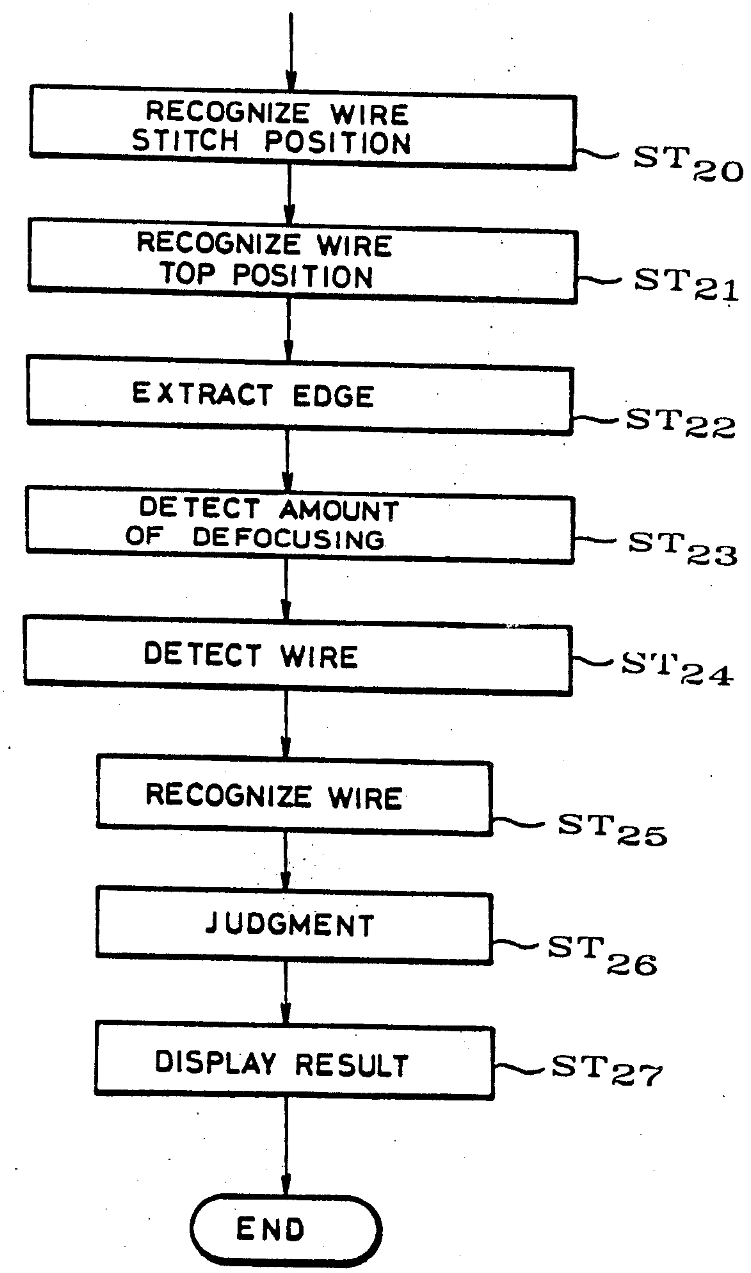

Next, the operation of the apparatus shown in FIG. 14 is described with reference to the flow chart shown in FIG. 17.

In Step $ST_{11}$, the diagonal illumination devices 59 are energized to emit light, and in Step $ST_{12}$, images $A_0$ and $B_0$ from the TV camera-A **62*a* and the TV camera-B 62*b*, respectively, are entered. Then, in Step $ST_{13}$, the emission of light from the diagonal illumination devices 59 are stopped, and in Step $ST_{14}$, the downcast illumination device 58 is energized to emit light. In Step $ST_{15}$, as in Step $ST_{12}$, images $C_0$ and $D_0$ from the TV camera-A 62*a* and the TV camera-B 62*b***, respectively, are entered.

Figure 18:
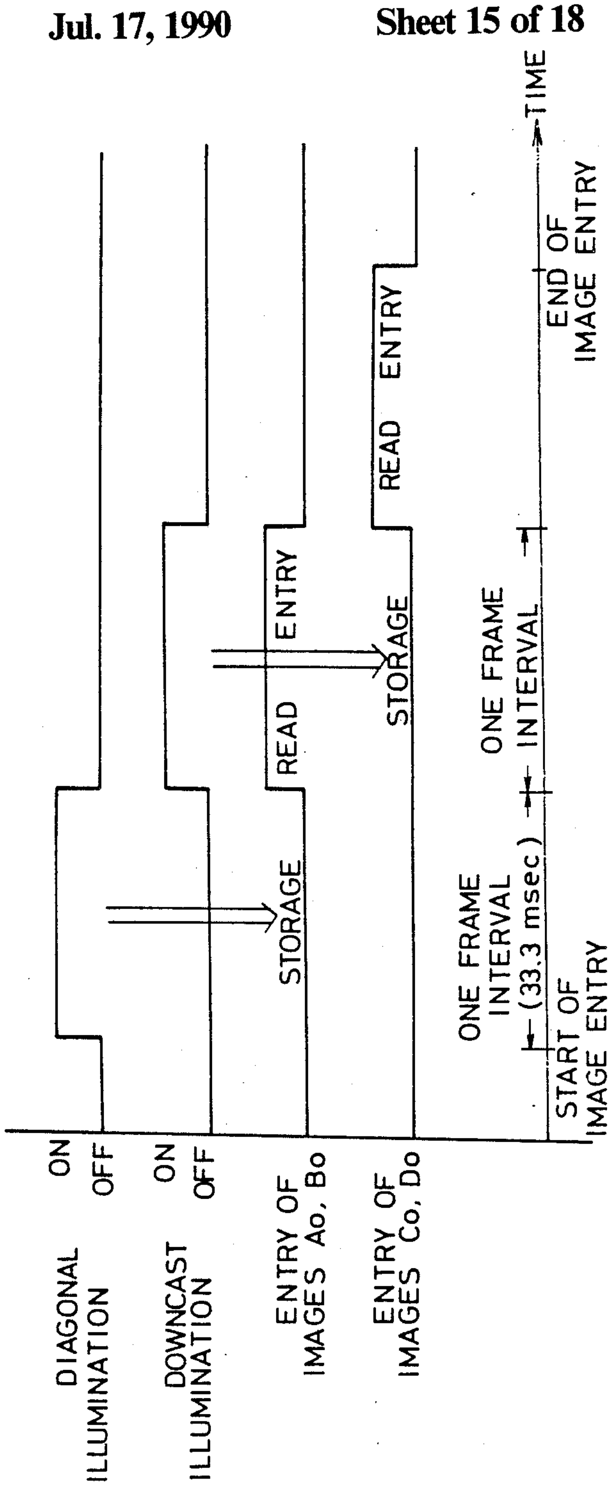
FIGS. 18 and 19 are time charts of image entry operation in the wire bond inspection apparatus of FIG. 14, in which different illumination means are used.
Figure 19:
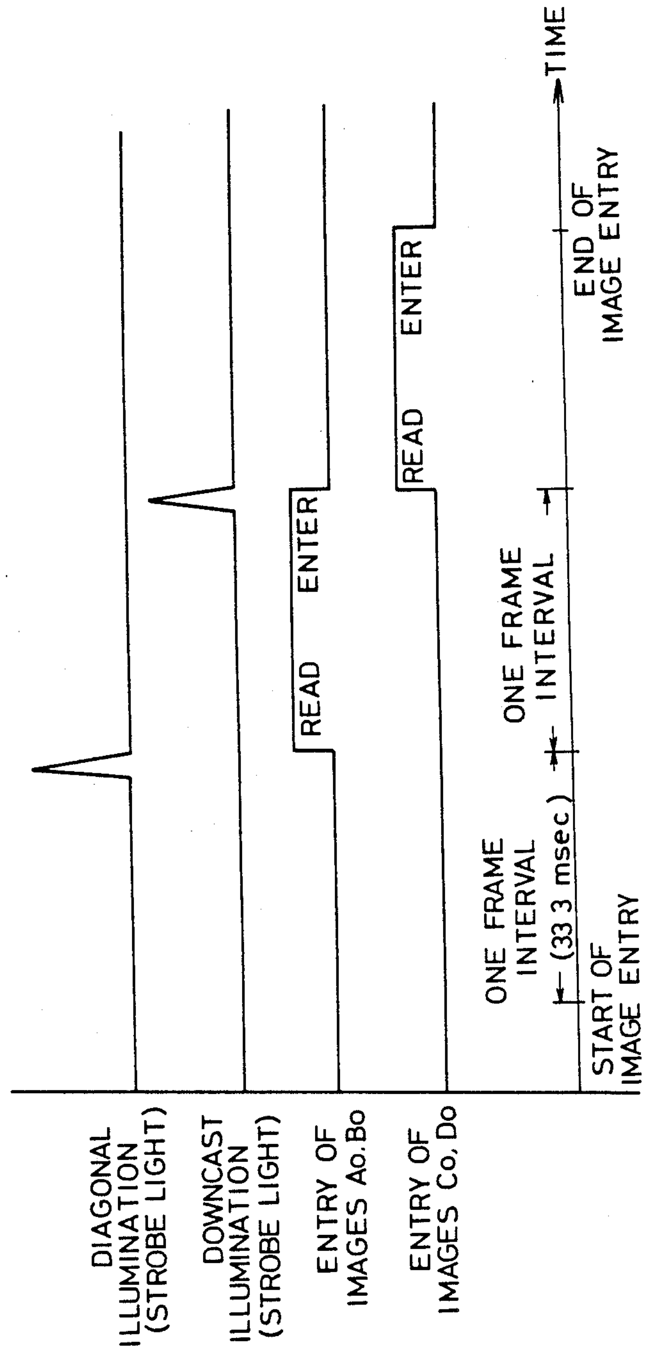

In Step $ST_{16}$, the downcast illumination device 58 is deenergized. FIGS. 18 and 19 are timing chart from Step $ST_{11}$ to Step $ST_{16}$. FIG. 19 is for an arrangement in which the illumination is provided by strobe light devices.

Figure 20A:
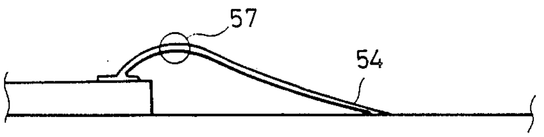
FIG. 20(*a*) is a side view of a normal curved wire, and FIG. 20(*b*) is a schematic representation of an image of the wire of FIG. 20(*a*) illuminated by the diagonal illumination means.
Figure 20B:
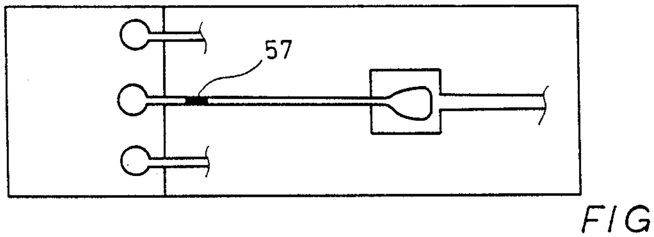
Figure 21A:
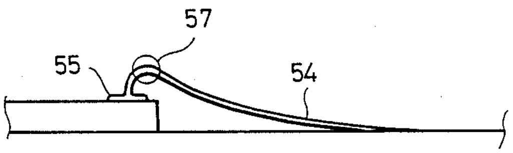
FIG. 21(*a*) is a side view of an undersirably bent wire, and FIG. 21(*b*) is a schematic representation of the image of the wire of FIG. 21(*a*) illuminated by the diagonal illumination means.
Figure 21B:
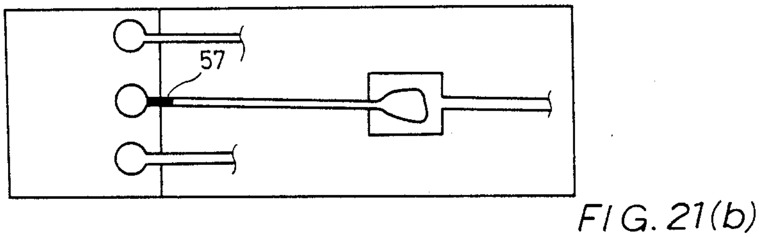
Figure 22A:
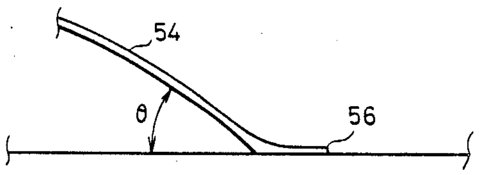
FIG. 22(*a*) is a side view of a wire portion near the stitch, and FIG. 22(*b*) is a schematic representation of the image of the wire portion of FIG. 22(*a*) picked up by the camera B shown in FIG. 14.
Figure 22B:
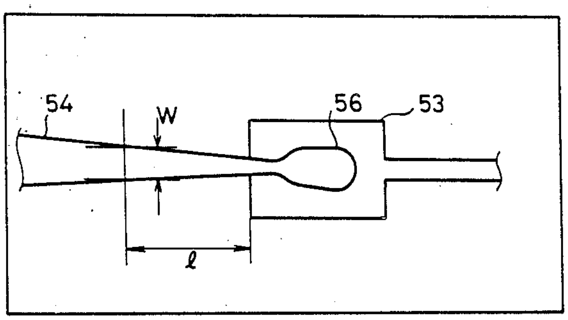

After that, in Step $ST_{17}$, the images $A_0$, $B_0$, $C_0$ and $D_0$ in the image memory 63 are converted into a binary form. The thus obtained images $A_1$, $B_1$, $C_1$and $D_1$ in binary form are stored separately from the original images in the memory and are subjected to succeeding processing in Steps $ST_{18}$–$ST_{21}$. In Step $ST_{18}$, a template matching technique is employed in an IC and substrate recognizing section 64, in which the positions of the IC chip 52 and the substrate are recognized from the images $A_1$ and $B_1$ and a reference pattern. In Step $ST_{19}$, a wire ball recognizing section 65 recognizes the position of the wire ball 55 from the image $A_1$ by the projection technique. From the image $B_1$, a wire stitch recognizing section 66 detects the position of the wire stitch 56 by means of the projection technique in Step $ST_{20}$. In Step $ST_{21}$, the images $C_1$ and $D_1$ are used in a wire top recognizing section 67 to recognize the wire top portion 57 by the projection technique. FIG. 20(*a*) is a side view of a normal curved wire, and FIG. 20(*b*) is a schematic representation of an image of the curved wire shown in FIG. 20(*a*) in which the wire top portion 57 appears with higher brightness due to illumination by the diagonal illumination devices 59. Also, FIG. 21(*a*) is a side view of a curved wire with a bent locating immediately above a wire ball 55, and FIG. 21(*b*) is the image of the wire of FIG. 21(*a*) illuminated by the diagonal illumination devices 59. The original images stored in the image memory 63 are further processed in Step $ST_{22}$ to produce edge images of the wire which are additionally stored in the image memory 63. Next, in Step $ST_{23}$, from the edge images, amounts of defocusing are determined in a defocusing amount recognizing section 68 and the angles of rising of the wire at the intersections with the focal planes are calculated. FIG. 22(*a*) shows a portion of the wire 54 near the wire stitch 56, and FIG. 22(*b*) schematically shows the image of the wire portion of FIG. 22(*a*) picked up by the TV camera-B 62*b* focused on the substrate. As shown in FIG. 22, the image of the wire 54 becomes less definite from the wire stitch 56 toward the wire ball 55, and, accordingly, the width of the wire image increases and the wire image contrast decreases. Accordingly, by measuring the wire width W at a given position l spaced from the intersection of the wire with the focal plane, or by measuring the wire image contrast at the position l, the rising angle $\theta$ of the wire 54 from the wire stitch 56 can be estimated.

Figure 23:
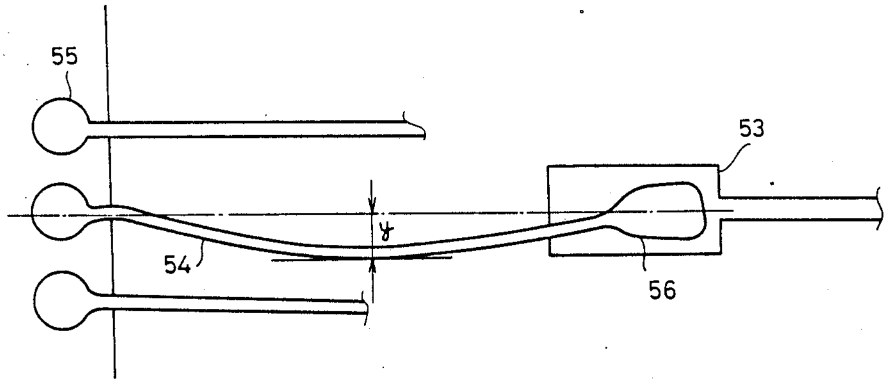
FIG. 23 is a schematic plan view for use in explaining how lateral displacement of a wire is measured.

Next, in Step $ST_{24}$, a wire detecting section 69 derives the contours of the wire in the form of a series of points from the edge images stored in the image memory 63 to thereby identify the wire portion 54 in the images. In Step $ST_{25}$, the series of points derived in Step $ST_{24}$ are traced in a wire recognizing section 70 to determine if there is a lateral displacement of the wire 54. FIG. 23 is a schematic plan view, showing that the wire 54 is laterally displaced by an amount y from the reference line connecting the centers of the wire ball 55 and the wire stitch 56. Data from the respective recognizing sections 64, 65, 66, 67, 68 and 70 are applied to a judgment section 71 in Step $ST_{26}$ for comparison with reference data which has been stored in the judgment unit beforehand, and judgment is made as to whether the wires are acceptable or must be rejected and also determination is made as to reasons for such rejections, if any. The result of the analysis is displayed on display means 72 in Step $ST_{27}$.

The control unit 60 controls the TV cameras 62*a* and 62*b*, the image memory 63, the recognizing sections 64, 65, 66, 67, 68 and 70, the judgment section 71, the downcast illumination device 48 and the diagonal illumination devices 59. The control unit 60 is preprogrammed to execute the sequence of from Step $ST_{11}$ to Step $ST_{27}$.

In the above-described embodiment, half-mirrors are used to make the optical axes for the image pickup systems coincident with each other, but prisms can be used instead for the same effects. Furthermore, two TV cameras are used in the described embodiment, three or more TV cameras may be disposed in the same coaxial optical system to inspect more complicated articles with higher precision.

In the above-described embodiment, a thermal printer head is an article to be inspected, but integrated circuit devices with lead frames which have no difference in level between the IC's and substrate can be inspected by the apparatus. Thus, the present invention can be used for wire bond defect detection for any types of integrated circuit devices with bonded wires.

As described, the inspection apparatus according to the present invention comprises a plurality of image pickup means which have their focal planes displaced from each other and are disposed to pick up the image of a wire to be inspected through a common optical system; illumination means having an optical axis coincident with the common optical axis of said image pickup means; diagonal illumination means for directing illuminating light diagonally to the wire; control means for controlling the light emitting timing of the respective illumination means; image storage means for digitizing outputs of the plurality of image pickup means and storing the digitized outputs in a plurality of image memory locations; an image processing unit for reading out contents of the image storage means and determining the positions of wire bonds and the positions of the top portion of the wire, the rising angles of the wire at the intersections with the respective ones of the focal planes of the image pickup means, and the lateral displacement of the wire; and a judgment unit for utilizing the result of the determination made in the image processing unit for making judgment as to whether the wire bonds are acceptable or to be rejected. With this inspection apparatus, even when wires are arranged densely, wire bond positions can be detected correctly, and the shape of the wire can be inspected in three dimensions so that undesirable bends, sagging, lateral leaning and like three-dimensional defects of the wires can be detected. Furthermore, the apparatus of the present invention can detect displacements of wire bends.

In the foregoing description, the term "wire" has been used, but the present invention is applicable not only to wires but also to any elongated articles like wires.

What is claimed is:

1. A method for determining the shape of a wire or like article positioned in a space, comprising the steps of:

splitting light from the article through an objective lens disposed to face said article into a plurality of optical paths;

deriving an image of said article by each of a plurality of image pickup devices which are disposed in the respective ones of said optical paths, said plurality of image pickup means being disposed at different distances from said objective lens and having their focal planes located in different positions;

processing the thus derived images of said article by means of image processing means to thereby measure the contrast and the width of the image of said article;

detecting the intersections of said article with said focal planes and also measuring distances of various points of said articles from said focal points; and interconnecting said intersections and said points of said article to thereby determine the shape of said spatially disposed article.

2. Apparatus for inspecting a bonded wire or like article, comprising:

a plurality of image pickup means having their focal planes disposed in different positions for picking up an image of said article via a common coaxial optical axis;

illuminating means having an optical axis coincident with said common optical axis of said image pickup means;

diagonal illuminating means for directing light diagonally to said article;

control means for controlling the timing of the emission of light from said respective illuminating means;

image storage means for digitizing outputs from said plurality of image pickup means and storing the digitized outputs in a plurality of image memory locations;

an image processing unit for reading out the contents of said image storage means to determine the position of connections of said article, the position of the top portion of said article, the rising angles of said article at the intersections of said article with said respective focal planes, and a lateral displacement of said article; and a judgment unit for utilizing the results of the determination made by said image processing unit for judging whether the bonding of said article is acceptable or not.

* * * * *